US011600394B2

(12) United States Patent
Rao et al.

(10) Patent No.: US 11,600,394 B2
(45) Date of Patent: Mar. 7, 2023

(54) COLLABORATION VIA CHAT IN HEALTH CARE SYSTEMS

(71) Applicants: INFINITE COMPUTER SOLUTIONS INC., Rockville, MD (US); INFINITE COMPUTER SOLUTIONS (INDIA) LIMITED, Bangalore (IN)

(72) Inventors: Sanjesh Rao, Haymarket, VA (US); Harish Pai, Ashburn, VA (US); Mohamed Madar Mohideen M Z, Chennai (IN)

(73) Assignee: ZYTER INC., Rockville, MD (US)

( * ) Notice: Subject to any disclaimer, the term of this patent is extended or adjusted under 35 U.S.C. 154(b) by 198 days.

(21) Appl. No.: 16/753,093

(22) PCT Filed: Oct. 3, 2018

(86) PCT No.: PCT/US2018/054121
§ 371 (c)(1),
(2) Date: Apr. 2, 2020

(87) PCT Pub. No.: WO2019/070822
PCT Pub. Date: Apr. 11, 2019

(65) Prior Publication Data
US 2020/0279658 A1    Sep. 3, 2020

Related U.S. Application Data

(60) Provisional application No. 62/567,359, filed on Oct. 3, 2017.

(51) Int. Cl.
*G16H 10/60* (2018.01)
*G16H 40/20* (2018.01)
(Continued)

(52) U.S. Cl.
CPC .............. *G16H 80/00* (2018.01); *G16H 10/60* (2018.01); *G16H 40/67* (2018.01); *H04L 51/046* (2013.01)

(58) Field of Classification Search
CPC ........ G16H 80/00; G16H 40/67; G16H 10/60; H04L 51/046
See application file for complete search history.

(56) References Cited

U.S. PATENT DOCUMENTS

2013/0124226 A1* 5/2013 Gedala ................... G16H 80/00
 705/3
2015/0350148 A1* 12/2015 Kenney ................... H04L 51/12
 709/206
(Continued)

OTHER PUBLICATIONS

Office action issued in European Application No. 18863334.0, dated Jun. 15, 2021, 8 pages.

*Primary Examiner* — Michael Tomaszewski
*Assistant Examiner* — Mohmad Muqueeth
(74) *Attorney, Agent, or Firm* — Dave Law Group LLC; Raj S. Dave

(57) ABSTRACT

According to an aspect of the present disclosure, a healthcare system receives a request to initiate a chat in relation to a patient, identifies healthcare providers having responsibility for the patient, and provides a chat session with the identified healthcare providers as participants. Upon receiving a command (requesting information on the patient) during the chat session, the healthcare system retrieves an electronic medical record (EMR) of the patient and sends the EMR to the participants of the chat session. In one embodiment, the command does not specify the identifier of the patient in the chat session. In another embodiment, when an external EMR system maintains EMRs of the patient, the healthcare system retrieves the EMR of the patient from the EMR system without requiring the participant to manually (Continued)

authenticate after specifying the command. Accordingly, the healthcare system is configured to facilitate collaboration among healthcare providers.

20 Claims, 9 Drawing Sheets

(51) Int. Cl.
  *G16H 80/00* (2018.01)
  *G16H 40/67* (2018.01)
  *H04L 51/046* (2022.01)

(56) References Cited

U.S. PATENT DOCUMENTS

| | | |
|---|---|---|
| 2016/0147971 A1 | 5/2016 | Kolowitz |
| 2016/0275247 A9 | 9/2016 | Schoenberg |
| 2017/0140105 A1 | 5/2017 | Smith |
| 2017/0178266 A1 | 6/2017 | Schmidt |

\* cited by examiner

| | Patient ID 511 | Patient Name 512 | HCP ID 513 | HCP Name 514 | Visit Date/Time 515 | Details 516 |
|---|---|---|---|---|---|---|
| 541 → | PT3007 | Ray, Andrew | HP049 | Joan Ames | 03/07/2017 10:30AM | Health care clinic |
| 542 → | PT4125 | Feinstein, Clara | HP052 | Anthony Amert | 03/21/2017 11:10AM | ........ |
| 543 → | PT3018 | Wang, Harry | HP013 | Katie Nelson | 03/29/2017 9:21AM | ........ |
| 544 → | PT4125 | Feinstein, Clara | HP020 | John Pemberton | 04/01/2017 12:15PM | Health care clinic |
| 545 → | PT3007 | Ray, Andrew | HP013 | Katie Nelson | 04/09/2017 10:46AM | ........ |
| 546 → | PT4125 | Feinstein, Clara | HP049 | Joan Ames | 05/06/2017 1:00 PM | ........ |
| 547 → | PT3018 | Wang, Harry | HP052 | Anthony Amert | 05/06/2017 3:00 PM | ........ |

COLLABORATION VIA CHAT IN HEALTH CARE SYSTEMS

CROSS-REFERENCE TO RELATED APPLICATIONS

This application is the U.S. national stage International Patent Application No. PCT/US2018/054121, filed on Oct. 3, 2018, which claims the benefit of priority to U.S. patent application No. 62/567,359, filed on Oct. 3, 2017, the disclosures of which are incorporated herein by reference in their entireties.

TECHNICAL FIELD

Embodiments of the present disclosure relate generally to healthcare systems and in particular to providing effective collaboration in such systems.

BACKGROUND

Healthcare systems aid the delivery of various healthcare aspects such as work-flow coordination, records management, diagnosis, etc., as is well known in the relevant arts. Healthcare systems are often employed by hospitals (healthcare delivery parties, in general) to aid various parties such as the medical staff and patients.

Collaboration refers to the process of facilitating multiple participants (e.g. healthcare personnel such as doctors, nurses, care team, etc.), who may be located in different geographical locations, to communicate among themselves by way of instant messaging, electronic mailing, file sharing, remote screen sharing, etc.

Aspects of the present disclosure are directed to providing effective collaboration in healthcare systems.

BRIEF SUMMARY

According to an aspect of the present disclosure, a healthcare system receives a request to initiate a chat in relation to a patient, identifies healthcare providers having responsibility for the patient, and provides a chat session with the identified healthcare providers as participants. Upon receiving a command (requesting information on the patient) during the chat session, the healthcare system retrieves an electronic medical record (EMR) of the patient and sends the EMR to the participants of the chat session. Accordingly, the healthcare system is configured to facilitate collaboration among healthcare providers.

In one embodiment, the command does not specify the identifier of the patient in the chat session. In another embodiment, when an external EMR system maintains EMRs of the patient and the command is received from a first participant, the healthcare system retrieves the EMR of the patient from the EMR system without requiring the first participant to manually authenticate after specifying the command.

According to one more aspect of the present disclosure, the healthcare system includes the EMR of the patient as a message of the chat session, thereby enabling the EMR of the patient to be stored as part of the history of the chat session in a non-volatile storage.

According to yet another aspect of the present disclosure, in response to receiving an indication to save the chat session, the healthcare system enables the participants of the chat session to edit a message of the chat session to form an edited message and stores the edited message in a non-volatile storage.

According to an aspect of the present disclosure, a healthcare provider using a client system sends a request to initiate a chat in relation to a patient, and participates in a chat session with healthcare providers as participants, the healthcare providers having responsibility for the patient. The healthcare provider, using the client system, sends a command during the chat session, with the command requesting information on the patient. In response to the command, an electronic medical record (EMR) of the patient is sent to the participants of the chat session. Accordingly, client system is configured to facilitate collaboration among healthcare providers.

In one embodiment, the healthcare provider (using the client system) does not specify the identifier of the patient as part of the command. In another embodiment, the healthcare provider shares the EMR of the patient without authentication after specifying the command.

According to one more aspect of the present disclosure, the client system displays the EMR of the patient as a message of the chat session, such that all the participants of the chat session are able to view the EMR details of the patient, and also enabling the EMR of the patient to be stored as part of the history of the chat session in a non-volatile storage. In one embodiment, the information is displayed only for a pre-configured time period (e.g. 10 seconds) in the chat session.

According to yet another aspect of the present disclosure, upon receiving an indication to save the chat session, the client system enables the healthcare provider to edit a message of the chat session to form an edited message and to send the edited message for storing in a non-volatile storage.

According to an aspect of the present disclosure, a third-party digital processing system (external to the healthcare system) receives a request for healthcare providers associated with a patient to initiate a chat in relation to the patient, identifies healthcare providers having responsibility for the patient, and sends the identified healthcare providers as being associated with the patient to facilitate a chat session to be provided with the healthcare providers as participants. Upon receiving another request requesting information on the patient in response to a command during the chat session, the third-party system retrieves an electronic medical record (EMR) of the patient and sends the EMR in response to receiving of another request to facilitate the EMR to be provided to the participants of the chat session. Accordingly, the third-party (external) digital processing system is configured to facilitate collaboration among healthcare providers.

In one embodiment, the command is received from a first participant and does not specify the identifier of the patient in the chat session. In another embodiment, the EMR of the patient is retrieved without requiring the first participant to manually authenticate after specifying the command.

According to another aspect of the present disclosure, the EMR of the patient is included as a message of the chat session, such that all the participants of the chat session are able to view the patient context information and also enabling the EMR of the patient to be stored as part of the history of the chat session in a non-volatile storage. In one embodiment, the information is displayed only for a pre-configured time period (e.g. 10 seconds) in the chat session.

According to yet another aspect of the present disclosure, the external system is an insurance server belonging to an insurance carrier, the insurance server maintaining information on patients having insurance coverage with the insurance carrier. According to one more aspect of the present disclosure, the external system is an enterprise server belonging to a third-party enterprise.

Several aspects of the invention are described below with reference to examples for illustration. However, one skilled in the relevant art will recognize that the disclosure can be practiced without one or more of the specific details or with other methods, components, materials and so forth. In other instances, well-known structures, materials, or operations are not shown in detail to avoid obscuring the features of the disclosure. Furthermore, the features/aspects described can be practiced in various combinations, though only some of the combinations are described herein for conciseness.

While the features of the present disclosure are described substantially in the context of healthcare services, it should be appreciated that several aspects of the present disclosure can be applied to other industries such as banking, telecommunication, transport, education, utilities and retail services.

BRIEF DESCRIPTION OF THE DRAWINGS

Example embodiments of the present disclosure will be described with reference to the accompanying drawings briefly described below.

FIG. 5 depicts portions of a visit summary data specifying the details of interactions between patients and healthcare providers in one embodiment.

In the drawings, like reference numbers generally indicate identical, functionally similar, and/or structurally similar elements. The drawing in which an element first appears is indicated by the leftmost digit(s) in the corresponding reference number.

DETAILED DESCRIPTION OF THE EMBODIMENTS OF THE DISCLOSURE

1. Example Environments

Figure 1A:
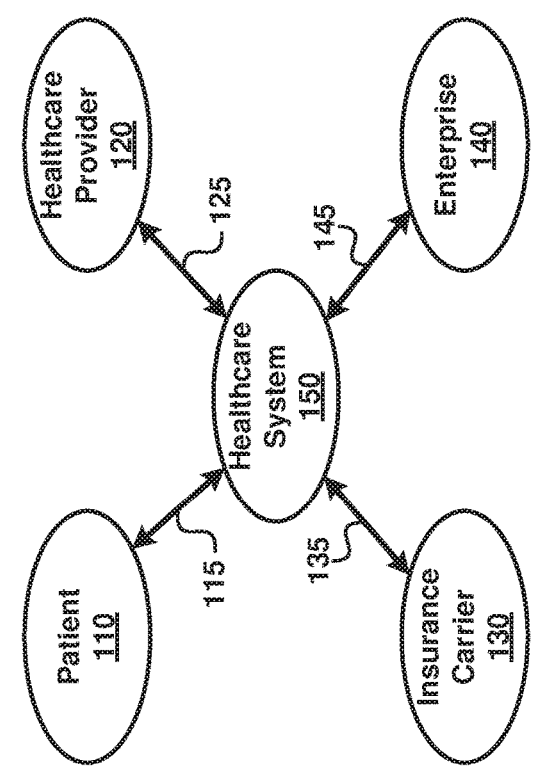
FIGS. 1A-1C depicts example environments in which several aspects of providing effective collaboration in healthcare systems can be implemented.
Figure 1B:
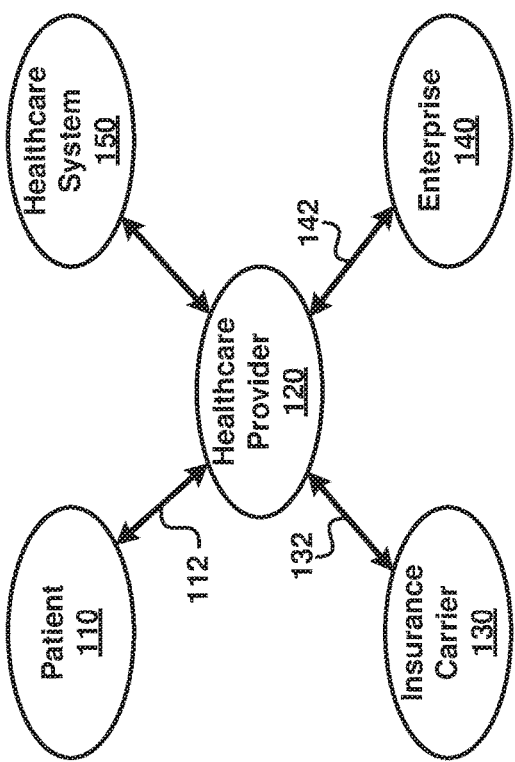
Figure 1C:
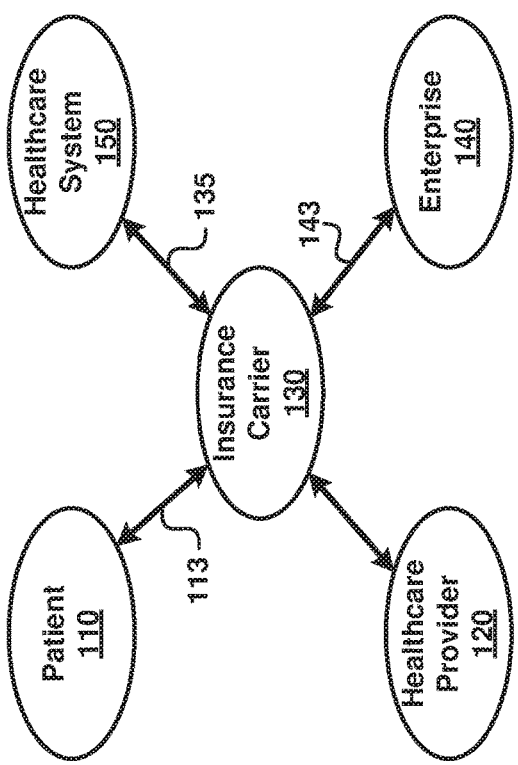

FIGS. 1A-1C depicts example environments in which several aspects of providing effective collaboration in healthcare systems can be implemented. The example environments are shown containing entities/elements such as patient 110, healthcare provider 120, insurance carrier 130, enterprise 140 and healthcare system 150. The elements are shown interconnected by data links 115, 125, 135, 145, etc.

Merely for illustration, only representative number/type of elements/links is shown in the Figure. Many environments often contain many more elements and/or links, both in number and type, depending on the purpose for which the environment is designed. Each element and data link of FIGS. 1A-1C is described below in further detail.

Patient 110 refers to a recipient of healthcare services. Information on patient 110 is commonly maintained in the form of electronic medical/health records (EMR/EHRs), as is well known in the relevant arts. EMR/EHRs (hereinafter referred commonly as EMRs) may specify details such as patient identity, dates of visit to avail healthcare services, symptoms of health problems faced by the patient, lab reports, etc.

Healthcare provider 120 refers to a physician/doctor, nurse, medical staff, care giver, etc. who provide one or more healthcare services to the patient. Healthcare providers are commonly associated with a healthcare organization (hospital, clinic, etc.) located at one or more geographical locations. Each healthcare provider commonly has responsibility for one or more patients.

Insurance carrier 130 represents an organization that offers various health insurance plans to patients, with each insurance plan being designed to protect the patient financially when health problems arise. In the below description, it is assumed that patient 110 has subscribed to at least one insurance plan offered by insurance carrier 130.

Enterprise 140 represents a third-party organization that is related to providing healthcare or management services (e.g. customer relationship management). Enterprise 140 generally operates data and applications independent of the other elements noted here.

Healthcare system 150 represents a system that assists a healthcare organization in the delivery of healthcare services to patients. Healthcare system 150 aids in various healthcare aspects such as work-flow coordination between healthcare providers and patients, records (such as EMR) management, diagnosis, etc., as is well known in the relevant arts.

Referring to FIG. 1A, healthcare system 150 receives a request to initiate a chat in relation to a patient. In one embodiment, the request is received from healthcare provider 120 (via data link 125) such as a physician/doctor. The chat request may be received when the physician wants to review the status of his/her patients or in response to patient 110 coming for check-up/review with the physician, either in-house or as an out-patient at a premises of the healthcare organization as is well known.

In alternative embodiments, the chat request may be received from patient 110 via data link 115, for example, when the patient wishes to discuss health related issues such as symptoms, diagnosis, medicines, etc. with any healthcare providers of the healthcare organization. The chat request may also be received from insurance carrier 130 via data link 135 or from enterprise 140 via data link 145, for example, when the insurance carrier/enterprise wishes to review the condition of a specific patient with the healthcare providers related to the patient.

Healthcare system 150 identifies healthcare providers having responsibility for patient 110. The identification may be performed in a known way, for example, by examining a visit summary data specifying the healthcare providers that had interacted with patient 110 during the previous visits. Healthcare system 150 may also identify additional personnel belonging to insurance carrier 130 or enterprise 140 who have responsibility for patient 110. Such identification may be performed by healthcare system 150 sending corresponding requests via data links 135 and 145 and receiving respective responses from insurance carrier 130 and enterprise 140 indicating the specific personnel related to the patient.

Healthcare system 150 provides a chat/collaboration session with the identified healthcare providers (and additional personnel) as participants of the chat session. After the chat session is initiated, each participant of the chat session is facilitated to send and receive (via data links 115, 125, 135 and 145) messages with the other participants in the chat session. The chat session facilitates the physician to discuss on the condition/medication of patient 110 with other healthcare providers/additional personnel.

In one embodiment, each of the identified providers/personnel (user) is sent an invitation (via data links 115, 125, 135 and 145) to join the chat session created in relation to the patient. Upon the invited users indicating acceptance of the invite, the accepting users are added as participants to the chat session.

Healthcare system 150 receives a command during the chat session, the command requesting information on the patient. The command may be specified in any convenient manner, for example, as a string forming part of text, by selection of a suitable user interface element, as a voice command, etc. The command may be received from patient 110 (via data link 115), healthcare provider 120 (via data link 125), personnel of insurance carrier 130 (via data link 135) or personnel of enterprise 140 (via data link 145).

Healthcare system 150 retrieves an EMR of the patient in response to receipt of the command. The EMR may be retrieved from an internal data store forming part of healthcare system 150. In one embodiment, healthcare system 150 sends a request for patient information via data link 145 to enterprise 140 and receives the EMR of the patient as a response to the request from enterprise 140 via data link 145. According to an aspect of the present disclosure, the participants of the chat session are facilitated to access the data/files on enterprise 140 without requiring the participants to sign into enterprise 140. Multiple EMRs from the different data stores may also be retrieved, with healthcare system 150 then forming a consolidated EMR of the patient from the retrieved data.

Healthcare system 150 then provides the EMR of the patient to the participants of the chat session as a response to the command. For example, healthcare system 150 may send the EMR of the patient in a format ready for display on systems used by patient 110 and/or healthcare provider 120. Each system then presents/displays the patient context information (EMR) as part of the chat session, such that all the participants of the chat session are able to view the patient context information. In one embodiment, the information is displayed only for a pre-configured time period (e.g. 10 seconds).

According to an aspect of the present disclosure, the patient context information is provided in the form of one or more messages of the chat session (similar to the other message manually sent by the participants via data links 115, 125, 135 and 145). By providing as messages, the patient context messages are facilitated to be saved/stored as part of chat history.

According to another aspect of the present disclosure, healthcare system 150 receives an indication to save/persist the chat session. The indication may be received from any one of the participants of the chat session via any one of data links 115, 125, 135 and 145. Saving the chat session implies that the messages (sent between the participants) of the chat session including the files exchanged between the participants, the patient context information retrieved and displayed as part of a message of the chat session, etc. be stored in a non-volatile storage (e.g. a data store forming part of healthcare system 150).

Healthcare system 150, in response to receiving the indication, enables the participants to edit a message of the chat session to form an edited message. In one embodiment, the list of messages exchanged in the chat session is displayed to each participant, with the participant then having the ability to delete one or more messages in the chat session prior to saving/persisting. Each participant may form a corresponding edited message with healthcare system 150 then forming a new message based on edited message received from the different participants of the chat session.

Healthcare system 150 stores the edited messages in a non-volatile storage such as the data store noted above. The stored edited messages represent the chat history and may be later retrieved during future chat sessions created in relation to the patient.

Thus, various healthcare providers (and additional personnel) are facilitated to effectively collaborate with each other in relation to a patient. It may be appreciated that the above interactions may be performed multiple times by the physician or other participants as part of the chat session. In addition, the participants typically send/receive messages during the chat session as part of a discussion about the patient based on the context information of the patient displayed as part of the chat session.

Referring to FIG. 1B, healthcare provider 120 sends a request (for example, using a client system) to initiate a chat in relation to a patient. The request to initiate the chat may be sent in response to receiving (via data link 112) a request from patient 110 for check-up/review with the healthcare provider. In alternative embodiments, the chat request may be sent in response to receiving corresponding requests for reviewing the condition of patient 110 from insurance carrier 130 (via data link 132) or from enterprise 140 (via data link 142).

Healthcare provider 120 then participates in a chat session with other healthcare providers as participants, the other healthcare providers having responsibility for the patient. Healthcare provider 120 sends a command during the chat session, with the command requesting information on the patient. In response to the command, an electronic medical record (EMR) of the patient is sent to the participants of the chat session. In one embodiment, healthcare provider 120 (using a client system) does not specify the identifier of the patient as part of the command. In another embodiment, healthcare provider 120 shares the EMR of the patient without authentication after specifying the command.

Referring to FIG. 1C, insurance carrier 130 (a third-party different from the first party healthcare system 150 and the second party healthcare provider 120) receives a request (from healthcare system 150 via data link 135) for healthcare providers associated with a patient to initiate a chat in relation to the patient, identifies healthcare providers having responsibility for the patient, and sends the identified healthcare providers as being associated with the patient to facilitate a chat session to be provided with the healthcare providers as participants. Insurance carrier 130 may notify patient 110 and/or enterprise 140 (via data links 113 and 143 respectively) of the one or more requests received from healthcare system 150.

Upon receiving another request requesting information on the patient in response to a command during of the chat session, insurance carrier 130 retrieves an electronic medical record (EMR) of the patient and sends the EMR in response to receiving of another request to facilitate the EMR to be provided to the participants of the chat session. In one embodiment, the command is received from a first participant and does not specify the identifier of the patient in the chat session. In another embodiment, the EMR of the patient is retrieved without requiring the first participant to manually authenticate after specifying the command.

Thus, the various entities/elements shown in FIGS. 1A-1C such as patient 110, healthcare provider 120, insurance carrier 130, enterprise 140 and healthcare system 150 are facilitated to effectively collaborate with each other in relation to a patient. The manner in which several features of the present disclosure can be implemented using a computing system (system architecture) is described below with examples.

2. System Architecture

Figure 2:
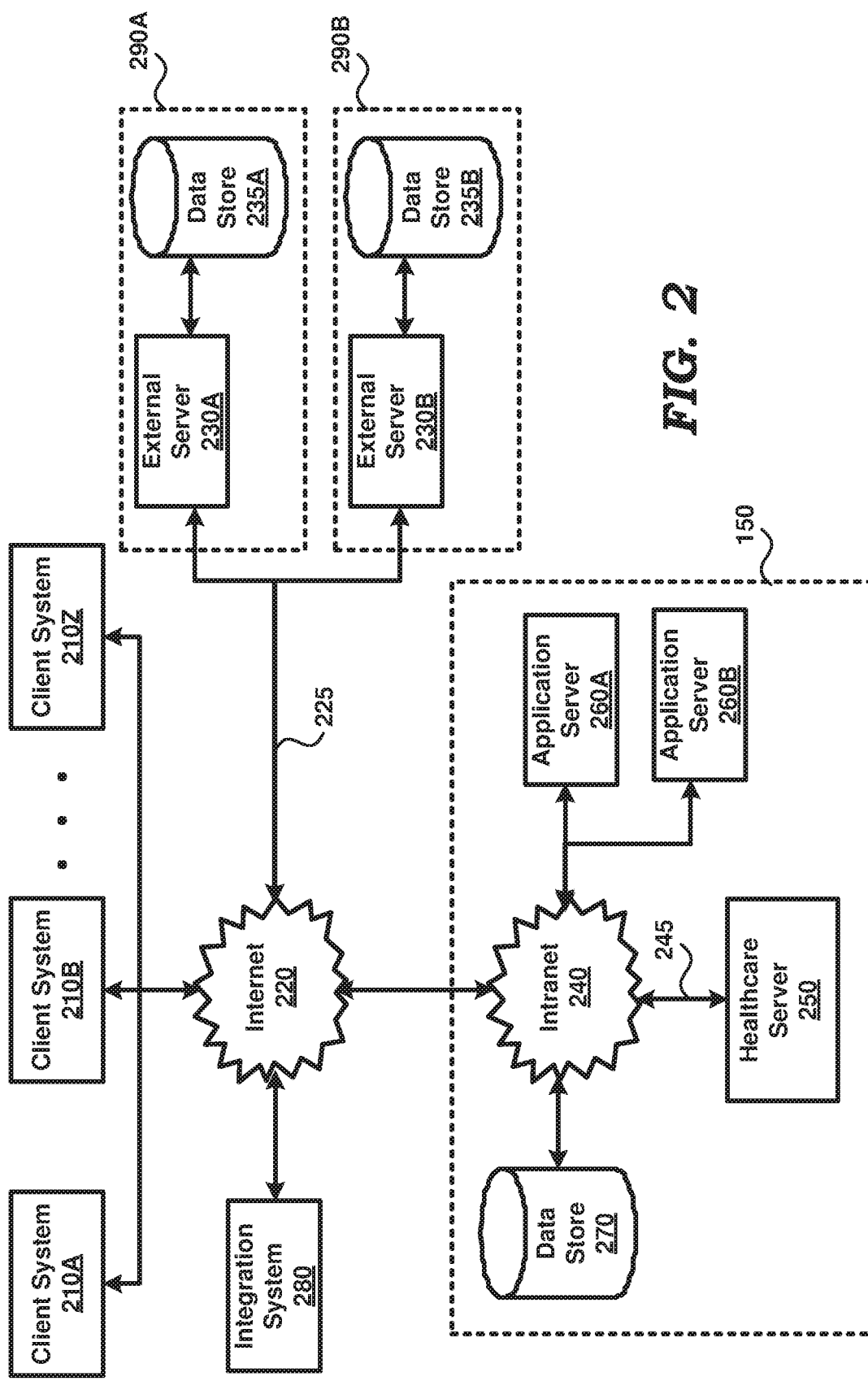
FIG. 2 is a block diagram of an example computing system in which several aspects of providing effective collaboration in healthcare systems can be implemented.

FIG. 2 is a block diagram of an example computing system in which several aspects of providing effective collaboration in healthcare systems can be implemented. The block diagram is shown containing client systems 210A-210Z, Internet 220, Intranet 240, external servers 230A-230B, data stores 235A-235B & 270, application servers 260A-260B, healthcare server 250 and integration system 280.

In one embodiment, healthcare server 250, application servers 260A-260B, and data store 270 along with intranet 240 operate together to as healthcare system 150 (as indicated by the dashed rectangle) that provides effective collaboration among various healthcare providers such as physicians/doctors, medical staff/nurse, care providers, etc.

Each of systems 290A (containing external server 230A and data store 235A) and 290B (containing external server 230B and data store 235B) represents a corresponding third-party external system with which healthcare system 150 interacts with to provide various aspects of the present disclosure. For example, external system 290A may represent a system provided by insurance carrier 130, with external server 230A being an insurance server belonging to insurance carrier 130. The insurance server may maintain (in data store 235A) information on patients having insurance coverage with insurance carrier 130. External system 290B may represent a system provided by enterprise 140, with external server 230B being an enterprise server belonging to enterprise 140.

Merely for illustration, only representative number/type of systems/devices are shown in the Figure. Many environments often contain many more systems and/or devices, both in number and type, depending on the purpose for which the environment is designed. Each system/device of FIG. 2 is described below in further detail.

Each of client systems 210A-210Z represents a system such as a personal computer, workstation, mobile station, mobile phones, computing tablets, etc., used by users/healthcare providers to send user requests to applications executing in healthcare system 150 (such as in application servers 260A-260B or healthcare server 250), and display the corresponding responses. The responses may be in the form of web pages and thus the requests may be in the form of Uniform Resource Locators (URLs) with appropriate additional content to specify the user requests. The users may generate the user requests based on appropriate user interfaces provided on each client system. In one embodiment, client systems 210A-210Z runs on different operating systems such as ANDROID™ and IOS™, and provide user interfaces using different web browser applications such as INTERNET EXPLORER®, SAFARI™ FIREFOX® and CHROME®.

Intranet 240 represents a network providing connectivity between application servers 260A-260B, healthcare server 250 and data store 270, all provided as part of healthcare system 150. Internet 220 extends the connectivity of these (and other systems of the healthcare system) with external systems such as client systems 210A-210Z and external systems 290A-290B. Each of intranet 240 and Internet 220 may be implemented using protocols such as Transmission Control Protocol (TCP) and/or Internet Protocol (IP), well known in the relevant arts. In general, in TCP/IP environments, an IP packet is used as a basic unit of transport, with the source address being set to the IP address assigned to the source system from which the packet originates and the destination address set to the IP address of the destination system to which the packet is to be eventually delivered.

A (IP) packet is said to be directed to a destination system when the destination IP address of the packet is set to the (IP) address of the destination system, such that the packet is eventually delivered to the destination system by Internet 220 and intranet 240. When the packet contains content such as port numbers, which specifies the destination application, the packet may be said to be directed to such application as well. The destination system may be required to keep the corresponding port numbers available/open, and process the packets with the corresponding destination ports. Each of Internet 220 and intranet 240 may be implemented using any combination of wire-based or wireless mediums.

Each of data stores 235A-235B and 270 represents a non-volatile (persistent) storage facilitating storage and retrieval of a collection of data by applications executing in corresponding server systems. For example, data store 270 facilitates applications executing in applications servers 260A-260B and healthcare server 250 to store/retrieve data related to patients, healthcare providers, the healthcare system, etc.

In one embodiment, each of data stores 235A-235B and 270 maintains information on patients in the form of EMRs. As noted above, EMRs may specify details of patients including patient identity, dates of visit, symptoms of medical problem faced by the patient, lab reports, patient records, etc. Each data store may also store the conversations of the participants of chat/interactive sessions between the various healthcare providers, the clinical data of the patients, etc.

Some of data stores 235A-235B and 270 may be implemented as a database server using relational database technologies and accordingly provide storage and retrieval of data using structured queries such as SQL (Structured Query Language). Some of data stores 235A-235B and 270 may be implemented as a file server providing storage and retrieval of data in the form of files organized as one or more directories, as is well known in the relevant arts.

Each of application servers 260A-260B, external servers 230A-230B and healthcare server 250 represents a server system, such as a web/application server, executing applications performing tasks requested by users (for example, using one of client systems 210A-210Z). Each server system may use data stored internally (for example, in a non-volatile storage/hard disk within the server system), external data (e.g., maintained in data store 235A-235B/270) and/or data received from external sources (e.g., from the user) in performing the requested tasks. The server system then sends the result of performance of the tasks to the requesting client system (e.g., one of 210A-210Z). The results may be accompanied by specific user interfaces (e.g., web pages) for displaying the results to the requesting user.

Integration system 280 represents a server system that facilitates healthcare server 250 to interact with external systems 290A-290B. Integration system 280 may accordingly provide integration APIs (Application Programming Interface) containing a library of interfaces/protocols to external systems, an integration database for storing information sent/received from external systems, and a web server that facilitates interaction with external systems that operate with text based protocols such as Hyper Text Transfer Protocol Secure (HTTPS) and WebSocket Secure (WSS).

In one embodiment, one or more healthcare providers (e.g. physicians) using client systems 210A-210Z are facilitated to take part in a chat session. Each healthcare provider is also facilitated to retrieve the information (EMR) related to a patient. However, to share such patient information, a healthcare provider is required to manually enter (using appropriate user interfaces) the patient information as one or more (chat) messages and send the messages to the other participants during the chat session. It may be appreciated that such manual entry may not be desirable, for example, when the patient context information is large.

Healthcare server 250, provided according to several aspects of the present disclosure, facilitates effective collaboration among healthcare providers while overcoming some of the drawbacks noted above. The manner in which healthcare server 250 (and accordingly healthcare system 150) provides effective collaboration is described below with examples.

3. General Flow

Figure 3:
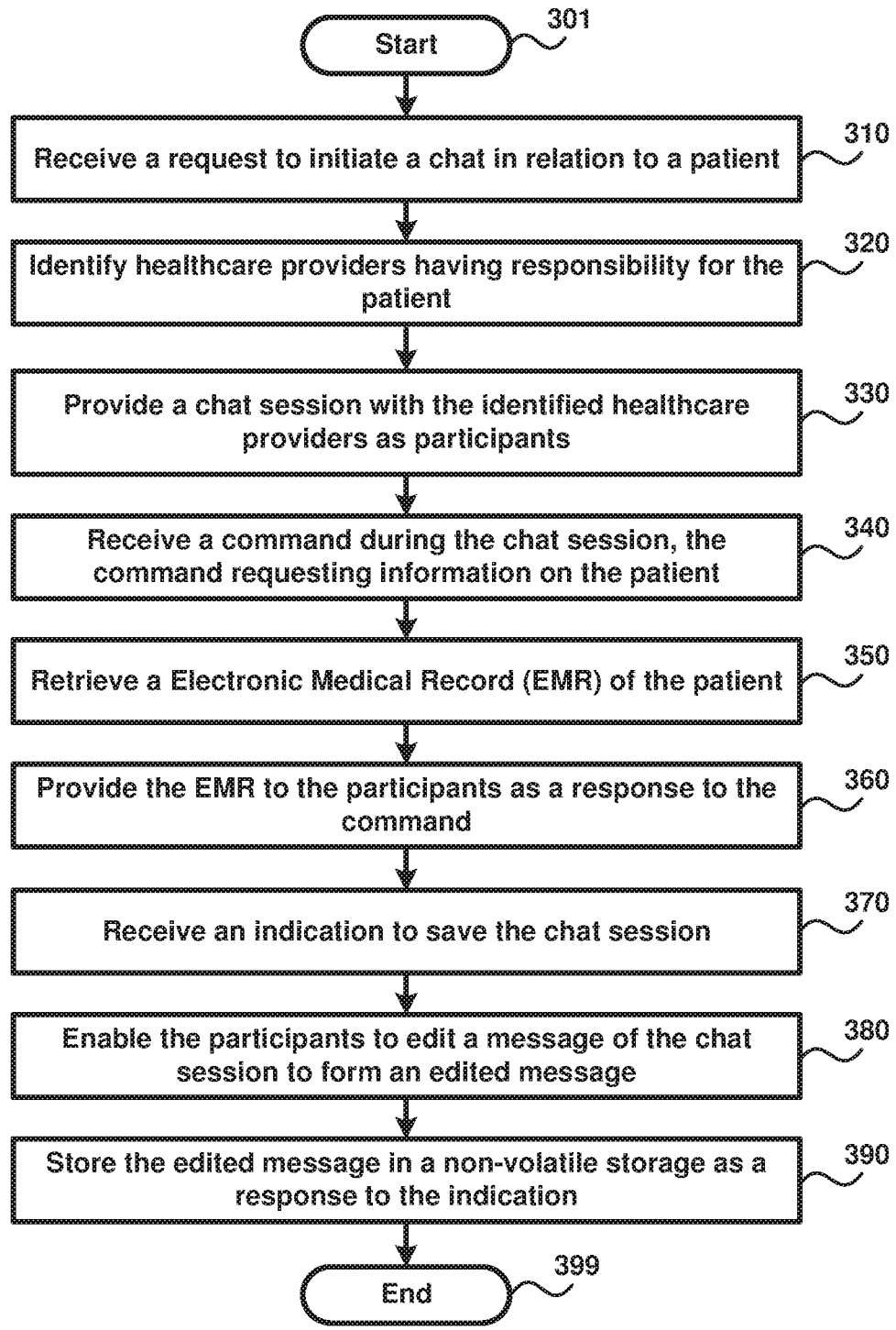
FIG. 3 is a flowchart illustrating the manner in which effective collaboration is provided in a healthcare system according to an aspect of the present disclosure.

FIG. 3 is a flowchart illustrating the manner in which effective collaboration is provided in a healthcare system (150) according to an aspect of the present disclosure. The flowchart is described with respect to healthcare server 250 of FIG. 2 merely for illustration. However, the features can be implemented in other systems and environments also without departing from the scope and spirit of various aspects of the present disclosure, as will be apparent to one skilled in the relevant arts by reading the disclosure provided herein.

In addition, some of the steps may be performed in a different sequence than that depicted below, as suited to the specific environment, as will be apparent to one skilled in the relevant arts. Many of such implementations are contemplated to be covered by several aspects of the present disclosure. The flow chart begins in step 301, in which control immediately passes to step 310.

In step 310, healthcare server 250 receives a request to initiate a chat in relation to a patient. The request may be received from one of client systems 210A-210Z by a user/healthcare provider such as a physician/doctor. The request may be received when the physician wants to review the status of his patients or in response to a patient coming for check-up/review with the physician, either in-house or as an out-patient as is well known.

In one embodiment, healthcare server 250 enables the user/physician to specify the details of the current visit of the patient, for example, based on the physical inspection/testing of the patient. During the visit, the user/physician decides to collaborate with other healthcare providers, for example, to discuss possible diagnosis and/or treatment of the patient, and accordingly initiates the chat session. In the following description, it is assumed that the user/physician is using client system 210A to send the request to initiate the chat.

In one embodiment, healthcare server 250 checks for validity of authentication details of the user/physician connecting via client system 210A. If authentication details of the user are found invalid, an authentication failed error message is displayed to the user. In addition, healthcare server 250 may allow the user to retry logging in for a predetermined number of times (which may be pre-configured). Control passes to step 320 if the authentication details of the user are found valid.

In step 320, healthcare server 250 identifies healthcare providers having responsibility for the patient. The identification may be performed by examining the data stored in data store 270 and/or interfacing with external servers 230A-230B. For example, a visit summary data may be examined to determine the specific set of healthcare providers that had interacted with the patient during the previous visits.

In step 330, healthcare server 250 provides a chat/collaboration session with the identified healthcare providers (previously visited/consulted by the patient) as participants of the chat session. A participant of the chat session implies that the healthcare provider is facilitated to send and receive from/view messages with the other participants in the chat session. The chat session facilitates the user/physician to discuss on the condition/medication of the patient (currently visiting the user/physician) with the other healthcare providers.

In one embodiment, each of the identified healthcare providers is sent an invitation to join the chat session created in relation to the patient. Upon the invited healthcare providers accepting the invite, the accepting healthcare providers are added as participants to the chat session. In the following description, it is assumed that the accepting healthcare providers are using a corresponding one of client systems 210B-210Z to participate in the chat session.

In step 340, healthcare server 250 receives a command during the chat session, the command requesting information on the patient. The command may be specified in any convenient manner, for example, as a string forming part of text, by selection of a suitable user interface element, as a voice command, etc.

In one embodiment, healthcare server 250 facilitates the user/physician to use custom commands to retrieve patient context information. A custom command represents a predefined string of characters that is understood by healthcare server 250 as indicating a corresponding action. Custom commands can be defined to have any convenient syntax. In an example implementation, "&Patient" is used as the custom command to retrieve the patient information. It may be readily observed that the custom command "&Patient" does not contain the identity details of the patient such as name of the patient, identity number of the patient, etc. and accordingly does not require the participants to remember the identity details of the patients.

In another embodiment, the messages (and correspondingly the command) sent during the chat session are voice messages/command. For example, instead of typing &Patient for retrieving patient data, a physician may say "Get Patient Details" as voice command, with healthcare server 250 in response identifying that a command requesting information on the patient has been specified as part of the chat session.

In step 350, healthcare server 250 retrieves an EMR of the patient in response to the custom command "&Patient". The EMR may be retrieved from data store 270 or from data stores 235A-235B by interfacing with external servers 230A-230B respectively. Multiple EMRs from the different data stores may also be retrieved, with healthcare server 250 then forming a consolidated EMR of the patient from the retrieved data. Such consolidation may involve operations such as validation, data mining and formatting on the data retrieved. The formatting may be according to the requirements of the client system sending the request (for example, based on whether client system 210A is a mobile device or a desktop computer), based on the preferences of the participants, etc.

In step 360, healthcare server 250 provides the EMR of the patient to the participants of the chat session as a response to the command ("&Patient"). For example, healthcare server 250 may send the EMR of the patient in a format ready for display on one or more of client systems 210A-210Z. Each client system then presents/displays the patient context information (EMR) as part of the chat session, such that all the participants of the chat session are able to view the patient context information. In one embodiment, the information is displayed only for a pre-configured time period (e.g. 10 seconds).

According to an aspect of the present disclosure, the patient context information is provided in the form of one or more messages of the chat session (similar to the other message manually sent by the participants). By providing as messages, the patient context messages are facilitated to be saved/stored as part of chat history.

Thus, various healthcare providers are facilitated to effectively collaborate with each other in relation to a patient, while relieving a participant/healthcare provider from the burden of manual entry of patient information. It may be appreciated that the steps of 340, 350 and 360 may be performed multiple times by the user/physician or other participants as part of the chat session. In addition, the participants typically send/receive messages during the chat session as part of a discussion about the patient based on the context information of the patient displayed in step 360.

In step 370, healthcare server 250 receives an indication to save/persist the chat session. The indication may be received from any one of the participants of the chat session using one of client systems 210A-210Z. Saving the chat session implies that the messages of the chat session (sent among the participants) including the files exchanged between the participants, the patient context information retrieved and displayed as a message of the chat session, etc. be stored in a non-volatile storage such as data store 270.

In step 380, healthcare server 250 enables the participants to edit a message of the chat session to form an edited message. In one embodiment, the list of messages exchanged in the chat session is displayed to a participant, with the participant then having the ability to delete one or more messages in the chat session prior to saving/persisting. Each participant may form a corresponding edited message with healthcare server 250 then forming a new message based on edited message received from the different participants of the chat session.

In step 390, healthcare server 250 stores the edited message in a non-volatile storage such as data store 270. The stored edited message(s) represents the chat history and may be later retrieved during future chat sessions created in relation to the patient. Control then passes to step 399 where the flowchart ends.

It may be appreciated that steps 330 through 360 operate to facilitate the participants in a chat session to access data/files on the external EMR databases without requiring the participants to sign into the external EMR/EHR databases, use custom commands (that do not require participants to remember patients' details) for retrieving data/files from chat history and external EMR/EHR databases based on the context. Thus, healthcare server 250 (healthcare system 150) aids in providing effective collaboration.

It may be further appreciated that the healthcare system 150 may provide the above described features to client systems 210A-210Z in any convenient manner. The description is continued illustrating the manner in which aspects of the present disclosure are implemented in an example graphical user interface of a collaboration session in an embodiment.

4. Sample User Interfaces

Figure 4:
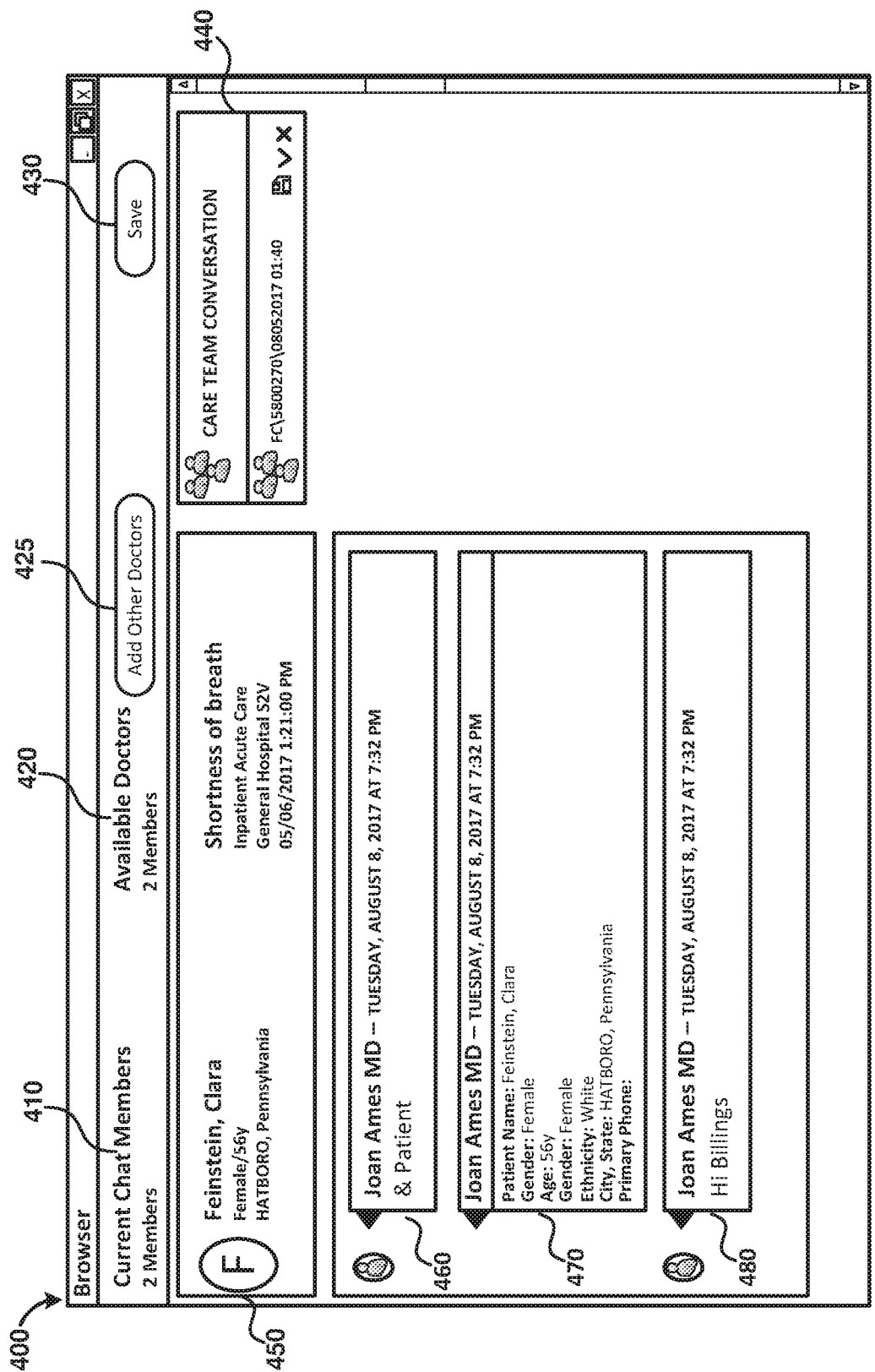
FIG. 4 illustrates an example graphical user interface (GUI) of a chat/collaboration session among multiple healthcare providers in an embodiment.

FIG. 4 illustrates an example graphical user interface (GUI) of a chat/collaboration session among multiple healthcare providers in an embodiment. A GUI entails aspects such as receiving of inputs from users for the application and displaying the outputs generated by the application, as is well known in the relevant arts. Furthermore, it may be appreciated that GUIs may be customized based on various factors (for example, based on whether the requesting client system is a mobile device or a desktop computer, based on the preferences of the participants, based on the branding guidelines of the customer/owner of the healthcare system, etc.).

Display area 400 represents a portion of a user interface displayed on a display unit (not shown) associated with one of client systems (assumed to be 210A, for illustration). In one embodiment, display area 400 corresponds to a web page rendered by a browser executing on the client system. Web pages are provided by healthcare server 250 in response to a user sending appropriate requests (for example, by specifying corresponding URLs in the address bar) using the browser.

For illustration, the description is continued assuming that display area 400 is being displayed on a system used by a healthcare provider/physician (who initiated the collaboration). It should be noted that user interfaces similar to display area 400 may be provided on all the client systems/devices used by the other participants of the chat session.

Display area 410 indicates the number of participants ("2") in the current chat session. Display area 420 indicates the number of available doctors/healthcare providers ("2") who could be added as participants in the chat session. Button 425 facilitates the user/physician to view and add new participants (doctors/physicians) to the current chat session from a list of doctors/physicians. Button 430 facilitates the user/physician to save a copy of the chat session (including messages 460, 470, 480) according to aspects of the present disclosure.

Display area 440 indicates the previous conversations of the user/physician in particular with the care team. Display area 440 may also contain relevant documents/files pertaining to the patient. A participant of the chat session may be allowed to review the past conversations and documents/files to understand the status of the patient better.

Display area 450 indicates a summary of the patient in respect of whom the current chat session has been initiated. Display area 450 is shown indicating the name of the patient to be "Feinstein, Clara". Each of display areas 460, 470 and 480 represents a corresponding message sent as part of the chat session. Display area 460 depicts the usage of custom command (&Patient) by one of the participants in the current chat session (Joan Ames) to retrieve the patient's details.

The retrieved patient's details are shown in display area 470. Upon reviewing retrieved patient's details, chat may be continued with other participants as shown in display area 480.

As may be readily appreciated from display areas 460 and 470, a participant can retrieve the information of a patient without having the necessity to enter details such as patient's ID etc. In addition, the patient related information is shown in display area 470 as a message of the chat session, thereby enabling the EMR of the patient to be stored as part of the chat history of the chat session in a non-volatile storage, if required (upon the user selecting button 430).

It may be appreciated that the above features of the present disclosure may be provided by healthcare server 250 based on data maintained in data stores 235A-235B/270. Sample data that may be maintained in such data stores is described below with examples.

5. Sample Data

FIG. 5 depicts portions of a visit summary data specifying the details of interactions between patients and healthcare providers in one embodiment. For illustration, the visit summary data are assumed to be maintained in the form of tables in data store 270. However, in alternative embodiments, the visit summary data may be maintained according to other data formats (such as files according to extensible markup language (XML), etc.) and/or using other data structures (such as lists, trees, etc.), as will be apparent to one skilled in the relevant arts by reading the disclosure herein.

Table 500 depicts visit summary data specifying the details of visits of different patients to the healthcare organization. In particular, column 511 "Patient ID" specifies a unique identifier associated with a patient and column 512 "Patient Name" specifies the name of the patient. Columns 513 "HCP ID" and 514 "HCP Name" respectively specify a unique identifier and the name of the healthcare provider who attended to (and provided a corresponding healthcare service) to the patient. Column 515 "Visit Date/Time" specifies the date and time of the visit of the patient, and column 516 "Details" specifies the details of the visit of the patient. Only a sample number of columns is shown in table 500, though in alternative embodiments, a large number of additional columns may be present to indicate additional details of the visit of the patient.

Each of rows 541-547 specifies the details of a corresponding visit by patients. It may be readily observed that rows 542, 544 and 546 specify the details of the visits by the patient having identifier "PT4125" (name "Feinstein, Clara"). Similarly, other rows specify the details of visits of other patients.

In response to receiving a request to initiate a chat in relation to a patient (assumed to be "PT4125" named "Feinstein, Clara" for illustration), healthcare server 250 inspects the visit summary data of table 500 and identifies healthcare providers having responsibility for the patient, that is, the healthcare providers who have treated the patient during earlier visits. As such, healthcare server 250 identifies the healthcare providers "HP052", "HP020" and "HP049" in rows 542, 544 and 546 as having responsibility for the patient "PT4125". It may be observed that the healthcare provider "Joan Ames" identified in row 546 is the user who sends the request to initiate the chat. Healthcare server 250 then provides a chat session with the identified healthcare providers "HP052", "HP020" and "HP049" as participants.

Upon receiving a command (requesting information on the patient) during the chat session, healthcare server 250 first determines that the current chat session has been created for patient "PT4125" and accordingly sends the unique identifier to external systems (290A-290B) as the basis for retrieving an electronic medical record (EMR) of the patient.

Thus, healthcare system 150 facilitates effective collaboration among healthcare providers using the visit summary data of table 500. The manner in which healthcare system 150 may be implemented is described below with examples.

6. Example Implementation

Figure 6:
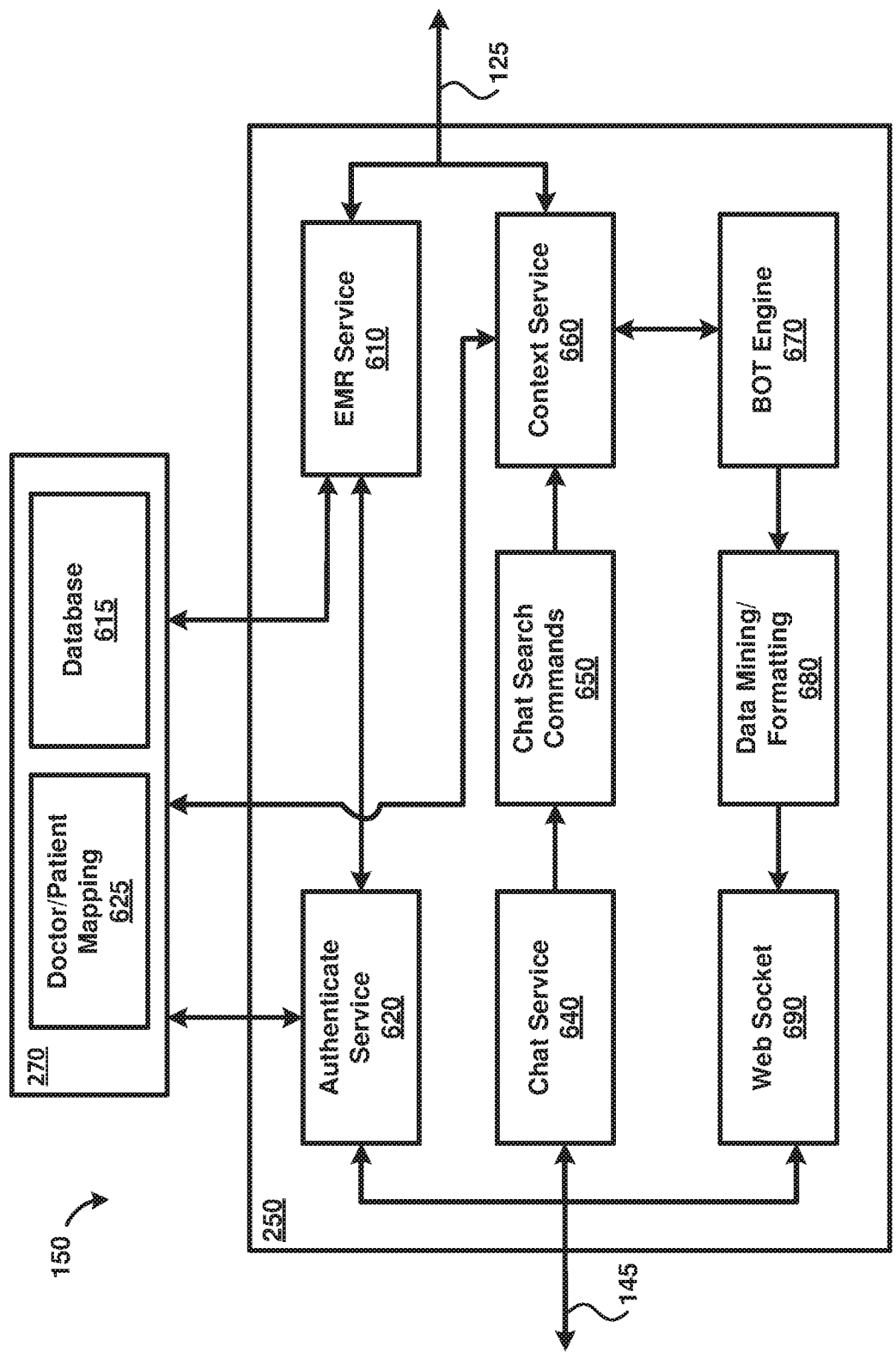
FIG. 6 is a block diagram illustrating an example implementation of a healthcare system.

FIG. 6 is a block diagram illustrating an example implementation of a healthcare system (150). The example implementation is shown in the form of a functional architecture containing multiple functional blocks implemented in various systems (such as healthcare server 250 and data store 270) belonging to healthcare system (150).

Healthcare server 250 is shown containing EMR service 610, authenticate service 620, chat service 640, chat search commands 650, context service 660, BOT engine 670, data mining/formatting 680 and web socket 690, while data store 270 is shown containing database 615 and doctor/patient mapping 625. It may be appreciated that in alternative embodiments, the various blocks/components may be implemented on multiple servers/data stores (which then together form healthcare system 150) as will be apparent to one skilled in the relevant arts. Each of the blocks of the healthcare system is described in detail below.

EMR service 610 facilitates accessing of data from external systems such as 290A-290B. For example, EMR service 610 may interact with the external systems such as integration system 280 to request for authentication/authorization tokens for accessing the external EMR/EHR data. Such authentication tokens may be stored in database 615 and later used when accessing the external EMR/EHR data.

Database 615 facilitates storing/retrieving of data by other blocks in the healthcare system based on SQL queries. Some examples of data that may be maintained in database 615 include, but not limited to, authentication token from EMR service 610, authentication data of the users/healthcare providers from authenticate service 620, doctor/patient mapping data 625, chat history of the participants from chat service 640 and context data from context service 660.

Authenticate service 620 facilitates authentication and/or authorization of the users/healthcare providers to avail the services of the healthcare system of the present disclosure. Authenticate service 620 may employ standard authentication and/or authorization techniques well known in the relevant art such as Active Directory, Single Sign On, Database and LDAP. Furthermore, security technologies known in the relevant art (such as SSL) may be used by authenticate service 620 during authentication and/or authorization. Authenticate service 620 may maintain user related data in database 615 for providing the authentication and/or authorization service.

Doctor/patient mapping 625 represents a mapping (data) between patients and doctors such as list of doctors consulted by a patient and/or list of patients treated by a doctor/healthcare provider. An example of such a mapping is the visit summary data shown in table 500 of FIG. 5. The doctor/patient mapping 625 may be updated periodically (for example, based on periodical examination of external EMR/EHR data). In addition, the mapping data may be updated by physician/healthcare providers during the visits by the patients.

Upon successful authentication and/or authorization of the user/healthcare provider, authenticate service 620 determines a list of patients handled by the authenticated user based on the information in doctor/patient mapping data 625 (as described in detail above). Authenticate service 620 then sends for display (for example, by sending the details to requesting client system 210A) the corresponding list of patients, thereby allowing the healthcare provider to access the profiles of his/her patients (including complete medical history, information related to last visit, appointments etc.).

Chat service 640 enables chat/collaboration among multiple participants of the healthcare system. Choosing/selecting a chat option for a particular patient enables an authenticated participant to discuss about a patient with other participants. In an example implementation, upon choosing the chat option, chat service 640 initiates a chat session by creating a group with all the participants (healthcare providers) having responsibility for the patient. Chat service 640 may use doctor-patient mapping data 625 for initiating the chat session. In addition, chat service 640 may store a chat history specifying the details of chats performed earlier in database 615. Chat service 640 also may identify and forward search commands issued by the participants during a chat session to chat search commands 650.

Chat search commands 650 enables the participants in a chat session to issue search commands for required information such as patient information, last vital information, patient/doctor visits, files etc. in chat history (stored in database 615) and/or external EMR/EHR databases and to receive/view the results of the search commands. Chat search commands 650 may accordingly interact with context service 660 to perform the desired searches indicated by the issued search commands, receive the results of the searches and provide the results as corresponding responses to the issued search commands.

Context service 660 enables other blocks/components of healthcare system to retrieve required data from database 615 and and/or external EMR/EHR databases based on a context. The context may be related to a specific patient, a specific healthcare provider, and/or the specific background (e.g. triaging, chat, etc.) in which the context service has been requested. Context service 660 receives requests from chat search commands 650 or BOT engine 670 indicating the specific data to be retrieved. Context service 660 may then retrieve the specific data requested from database 615 and/or external EMR/EHR databases (235A-235B) and forwards the retrieved data as corresponding responses to the requests.

BOT engine 670 provides an execution environment for executing bots/automated programs that perform a predefined set of actions, possibly by interacting with other systems such as client systems 210A-210Z. Some bots run automatically, while others only execute commands when they receive specific inputs. Examples of bots are web crawlers, chat room bots etc. Some of the bots may also facilitate predictive analytics using predictive algorithms. For example, in the field of healthcare, a patient info bot may pull the complete information/data of a patient from a database (which can be EMR/EHR and may act on the data to find some relevant/meaningful information and advice a doctor/healthcare provider with suggestions about the areas of treatment).

In one embodiment, a chat bot (executing in BOT engine 670) performs predictive analytics (using predictive algorithms) on chat/collaboration history, chat context and commands given by participants during a chat/collaboration session, and render the results/suggestions to the participants. For example, when a participant sends a message (typically in the form of message) in a chat session indicating that a patient is suffering from high fever, headache, rash, muscle and joint pain, a chat bot may search for the symptoms in chat/collaboration history (related to all patients) and may thereafter arrive at the suggestion that the patient might be suffering from dengue fever (diagnosis). The chat bot may also suggest possible medications for the diagnosis.

Data mining/formatting 680 provides both mining and formatting services such as formatting/modifying the results of the predictive analytics of bot engine 670 according to the requirements of client systems 210A-210Z, and send the formatted output (e.g. in the form of a report) to the client systems via web socket 690, thereby enabling client systems 210A-210Z to render the formatted output to the participants.

In addition, data mining/formatting 680 may also inspect the data received from bot engine 670 and determine additional insights/suggestions using mining algorithms well known in the art. For example, data mining/formatting 680 may identify additional data to be included to the data received from bot engine 670.

Web socket 690, well-known in the relevant arts, is a computer communications protocol, providing full-duplex communication channels over a single TCP connection, and facilitates peer to peer and client-server communication. Web socket 690 facilitates the collaborative communication among the participants (here healthcare providers). Also, web socket 690 facilitates data mining/formatting 680 to send the results/suggestions received from bot engine 670 to participants using client systems 210A-210Z.

It may be appreciated that the various components of FIG. 6 facilitate a healthcare system (150) to provide several aspects of the present disclosure. According to an aspect of the present disclosure, chat service 640 provides an effective and seamless collaboration among the participants of a chat/collaboration session, by obviating the necessity of the participants signing into external EMR/EHR databases (third-party databases) for accessing the data/files stored on the external EMR/EHR databases during the chat/collaboration session. As noted above, EMR service 610 generates authentication tokens for external EMR/EHR databases, and thereafter uses the tokens during the chat session to provide access to data/files stored on the external EMR/EHR databases.

According to one more aspect of the present disclosure, chat search commands 650 facilitates participants of a collaboration session to search for data/files by issuing search commands that do not require the participants to remember the details of the patients such as name of the patient, identity number of the patient, etc. According to another aspect of the present disclosure, chat search commands 650 in operation with context service 660 provides retrieval of meaningful and relevant information (data/files) based on the context in which the search commands are used.

The manner in which the various components of healthcare server 250 shown in FIG. 6 operate to provide effective collaboration among healthcare providers is described below with examples.

7. Sequence Diagram for Effective Collaboration

Figure 7:
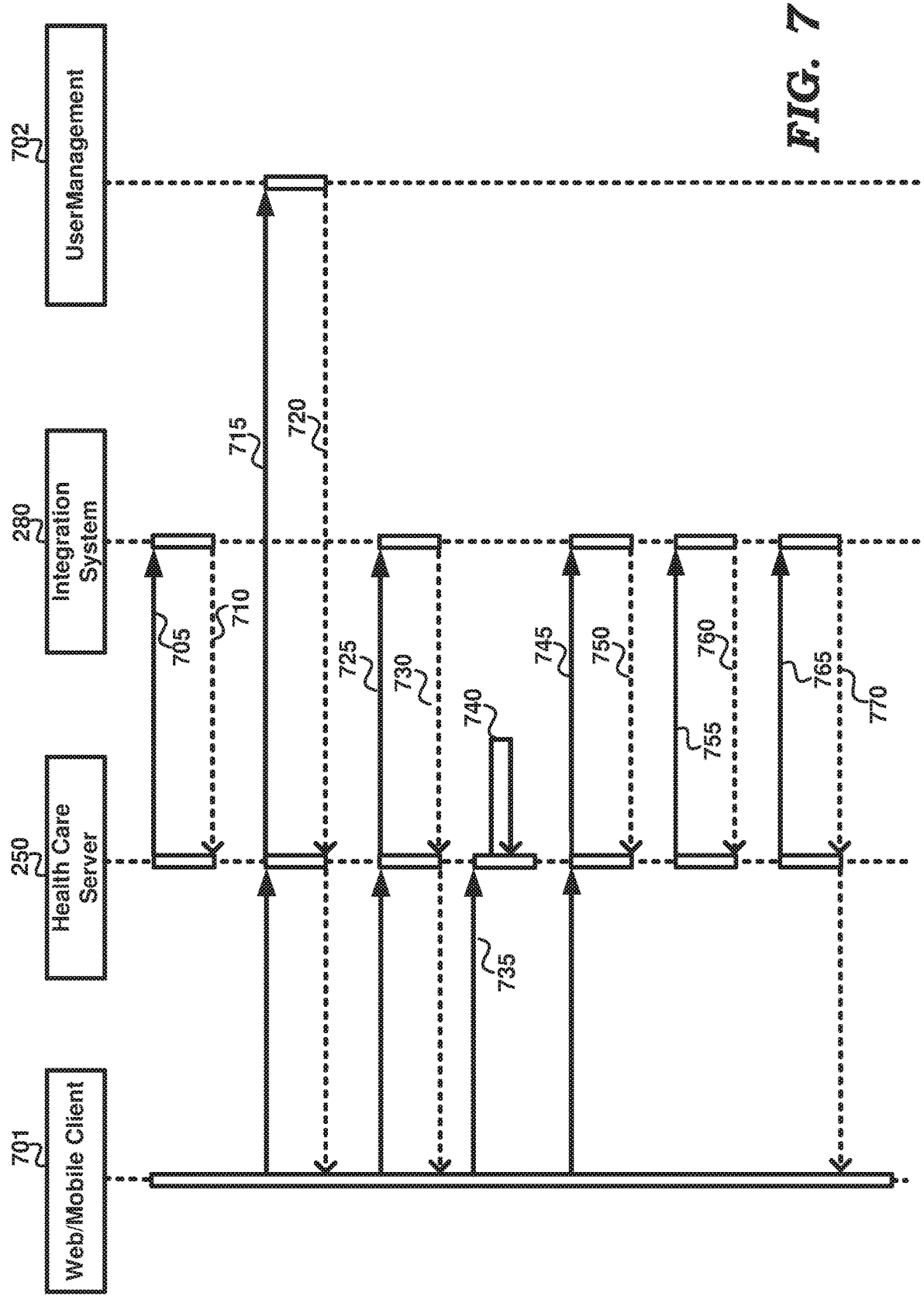
FIG. 7 is a sequence diagram illustrating the manner in which effective collaboration with context awareness is provided by a healthcare system in one embodiment.

FIG. 7 is a sequence diagram illustrating the manner in which effective collaboration with context awareness is provided by a healthcare system (150) in one embodiment.

The interactions are shown between web/mobile client 701 (executing in client system 210A), healthcare server 250, integration system 280 and user management system 702. It may be appreciated that though user management system 702 is shown as a separate system, the same may be implemented as a part of healthcare server 250. The interactions are described in detail below.

At 705, healthcare server 250 sends a request to integration system 280, requesting an authentication token/key to access an external EMR/EHR database (such as 290A-290B). Integration system 280 may then interact with the external EMR/EHR database and obtain the authentication token. At 710, integration system 280 sends the authentication token to healthcare server 250, using which healthcare server 250 is thereafter facilitated to access the EMR/EHR data stored in the external EMR/EHR database. Healthcare server 250 may store the authentication token in database 615 for subsequent usage.

At 715, web/mobile client 701 sends a user authentication request to healthcare server 250 when a user/physician enters his/her authentication details at web/mobile client 701. Healthcare server 250 then forwards the user authentication request to user management system 702. At 720, user management system 702 performs the validation of the authentication details contained in the user authentication request, and sends the results of validation as a response to the user authentication request to healthcare server 250, which in turn forwards the response to web/mobile client 701. Upon the response indicating an error in validation of the authentication details, web/mobile client 701 displays an error message to the user/physician.

The description is continued assuming that the response indicates successful validation of the user/physician. The user/physician may thereafter perform additional activities and then initiate a chat conversation/collaboration session with other physicians. Accordingly, the user/physician may be shown the user interface of FIG. 4 on web/mobile client 701, and the user/physician may thereafter exchange messages with the other participants of the chat/collaboration session.

At 725, web/mobile client 701 sends a patient info request to healthcare server 250 when the user/physician specifying custom command "&Patient" in display area 460 of FIG. 4. Healthcare server 250 then forwards the patient info request to integration system 280, along with the authentication token retrieved from database 615. Integration system 280 interacts (using the authentication token) with the external EMR/EHR database noted above to retrieve the requested patient information.

At 730, integration system 280 sends the retrieved patient information as a response to the patient info request. Healthcare server 250 receives the retrieved patient information from integration system 280 and manipulates the received patient information (for example, to suit the formatting requirements of web/mobile client 701) and sends the manipulated output to web/mobile client 701. Web/mobile client 701 displays the manipulated output (formatted patient information) to user/physician as shown in display area 470 of FIG. 4.

As noted above, the various participants in the chat session may exchange messages using interfaces similar to FIG. 4 provided on corresponding one of client systems 210A-210Z. The manner in which such messages are processed is described in detail below.

At 735, web/mobile client 701 forwards a message to healthcare server 250 when the user/physician enters the message in the user interface of FIG. 4. At 740, healthcare server 250 receives the message from web/mobile client 701 and forwards the same to other client systems used by the other participants of the chat session. In an embodiment, where multiple instances of healthcare server 250 are active (such as FIG. 8 described below) or where the participants belong to multiple EMR systems are connected to other application servers, healthcare server 250 forwards the message received from web/mobile client 701 to the other healthcare servers, which in turn forwards the message to the client systems used by participants. Furthermore, healthcare server 250 receives messages from the other client systems and forwards the messages to web/mobile client 701, which then displays the messages in user interface of FIG. 4.

It may be appreciated that the above noted actions at 725 and 730 are performed in view of the authentication token being valid and accordingly being recognized by the external EMR/EHR database. However, such authentication token are often valid only for a fixed period and are considered expired after the fixed period. The manner in which an expired authentication token is handled when processing a request for EMR/EHR data is described in detail below.

At 745, web/mobile client 701 sends a last vital info request to healthcare server 250 when the user/physician specifies a corresponding custom command (e.g. "&LastVital"). Healthcare server 250 then forwards last vital info request to integration system 280, along with the authentication token retrieved from database 615. Integration system 280 interacts (using the authentication token) with the external EMR/EHR database to determine that the authentication token has expired. At 750, integration system 280 accordingly sends a response to the last vital info request indicating that the authentication token has expired. At 755, healthcare server 250 sends a request for authentication token to integration system 280 and in response, at 760, integration system 280 sends a new authentication token to healthcare server 250. Actions performed at 755 and 760 are similar to the actions performed at 705 and 710 and accordingly their description is not repeated here for the sake of conciseness.

Upon receiving the new authentication token, at 765, healthcare server 250 resends the request for last vital info along with the new authentication token to integration server 290. At 770, integration system 280 sends a response to healthcare server 250, which in turn forwards to web/mobile client 701 after performing suitable manipulation. Actions performed at 765 and 770 are similar to the actions performed in 725 and 730 and the description is not repeated here for the sake of conciseness. Thus, the EMR/EHR data is provided access during the chat session even when the previously generated authentication token has expired.

It may be appreciated that the operation of FIGS. 2 through 7 facilitates the healthcare system to provide effective collaboration among the healthcare providers present in the healthcare system.

It may be further appreciated that the features of the present disclosure are described above assuming that the healthcare system is implemented on a single server (healthcare server 250 of FIG. 2). However, healthcare systems are typically implemented using multiple servers and data stores. The manner in which a healthcare system may be provided using a cloud infrastructure is described below with examples.

8. Healthcare System Using Cloud Infrastructure

Figure 8:
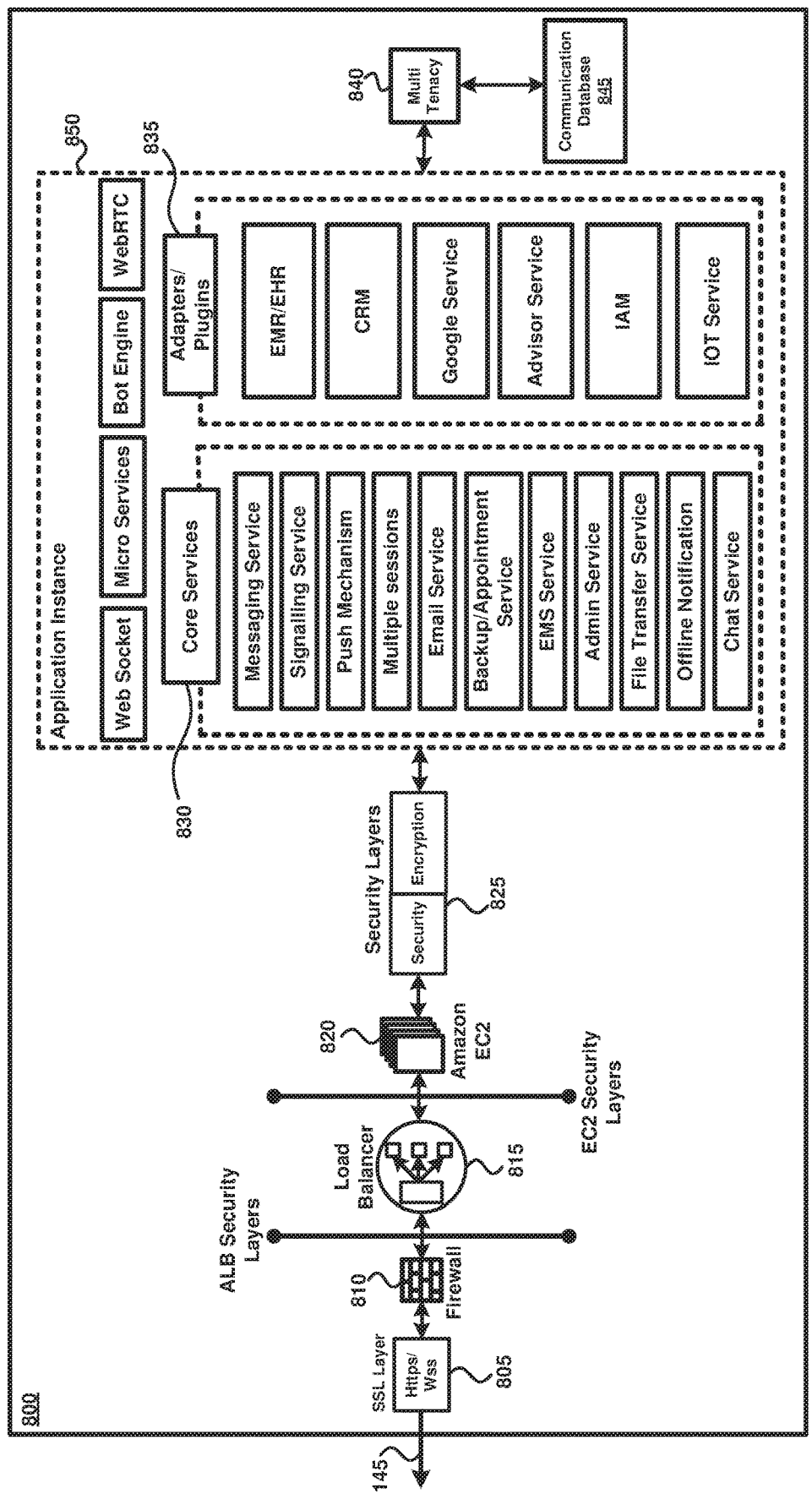
FIG. 8 is a block diagram illustrating the manner in which a healthcare system is provided using a cloud infrastructure in an embodiment.

FIG. 8 is a block diagram illustrating the manner in which a healthcare system is provided using a cloud infrastructure in an embodiment. Specifically, the healthcare system is shown implemented using AWS (Amazon Web Services) framework 800 available from Amazon™. Accordingly, the block diagram is shown containing SSL (Secure Sockets layer) 805, firewall 810, load balancer 815, Amazon Elastic Compute Cloud (Amazon EC2) 820, security layers 825, application server (instance) 850, and multi tenancy 840.

It should be appreciated that the healthcare system is implemented using multiple (typically, 50-100) application servers, though only a single application server 850 is shown in FIG. 8 for clarity.

SSL 805 is a standard security technology for establishing an encrypted link between application server 850 and any of client systems 210A-210Z. Firewall 810 is a network security device that monitors traffic to or from a network. Firewall 810 also allows or blocks traffic based on a defined set of security rules. Amazon EC2 820 is a web service that provides secure, resizable compute capacity on the cloud. Application Load Balancer (ALB) 815 distributes the user requests among the various application servers for reasons such as scalability, fault tolerance, etc. Security layers 825 provide additional level of security for the healthcare system in addition to SSL 805 and firewall 810. Multi tenancy 840 handles the tenancy of healthcare system in Amazon EC2 820.

Application server 850 is shown containing core services 830 and adapters/plugins 835 (in addition to associated components such as web socket, micro services and bot engine described above with respect to FIG. 6). Core services 830 facilitate the interaction among one or more application servers and also the interaction with client systems 210A-210Z, while adapters/plugins 835 facilitate application server to interact with external systems (via integration system 280). Some of core services 830 and adapters/plugins 835 are described in detail below.

Messaging service enables messages to be sent among application servers and/or client systems 210A-210Z. Such messages may be encrypted using user keys. Signaling service is used to provide audio/video calls for collaboration among participants on client systems 210A-210Z. Such audio/video calls may be provided using WebRTC, WebSocket and Amazon EC2 820. Push mechanism pushes messages such as alerts or emergency notifications to the client system used by the appropriate user (here doctor/nursing staff). Multiple sessions service enables a user to login into multiple client systems simultaneously. Email service enables a user to compose and send emails including any attachments if any.

Backup/appointment service enables user to assign another user as back up (in cases of emergency) on his/her unavailability. In addition, backup/appointment service sends alerts or emergency notifications to another user assigned as back up. Furthermore, backup/appointment service enables recording of appointments for patient's consultations. As an example, recording of appointments includes modifying date, time and doctor mapped for consultation.

EMS (Enterprise Messaging Service) service provides multi factor authentications for users. For example, a two-factor authentication (two levels of verification) of login details of a user may be provided. Details of such two levels of verification are sent via emails, SMS (Short Messaging Service), etc. Admin service enables a user to fetch data from PHI (Protected Health Information) systems via integration system 280. File transfer service enables a user to send/share documents to another user in real time, for example, during collaboration. In addition, file transfer service may encrypt the documents before sending/sharing.

Offline notification service sends alerts to a user notifying emergency when client systems 210A-210Z are in offline mode. Offline notification service uses Firebase/APNs (Apple Push Notification Service) to send the alerts, for example, in the form of alarm beeps. Chat service enables chat-based collaboration among multiple participants including sending of private messages, creating chat rooms/groups and storing the chat history.

EMR/EHR adapter enables retrieving of EMR of patients from external EMR/EHR systems via integration system 280. Exemplary data in EMR includes patient documents, medications, patient info, care plan, doctor notes, observations, clinical summary and visits details. CRM adapter facilitates data to be retrieved from an external CRM system via integration system 280. Google™ service adapter facilitates application server 850 to interface with Google™ services. Advisor service adapter facilitates interactions with third party bots to retrieve suggestions and recommendations. IAM (Identity and Access Management) adapter facilitates interactions with external servers to perform authentication and/or authorization of the users/healthcare providers in the healthcare system.

IoT service adapter facilitates interactions with IoT devices such as heart monitors. Such interaction may facilitate application server 850 to determine whether heartbeat of a patient monitored through an IoT device records a lower value or a higher value than the standard thresholds, and then send an alert to the appropriate medical staff (nurse/doctor).

Additional components such as Micro services, WebRTC, Web sockets and Bot engine may be associated with application server 850. Micro services are back end services or self-sustained services and these can be any plug and play services. For example, in healthcare industry, the micro services render the patient data required by the doctors. WebRTC ((Web Real-Time Communication) provides web browsers and mobile applications with real-time communication (RTC) via simple application programming interfaces (APIs). WebRTC allows audio and video communication to work inside web pages by allowing direct peer-to-peer communication, eliminating the need to install plugins or download native apps. Web socket and Bot engine are described above with respect to FIG. 6.

Communication database 845 represents a non-volatile (persistent) storage facilitating storage and retrieval of data by applications executing in other systems such as application server 850. Communication database 845 may be implemented as a database server using relational database technologies and accordingly provide storage and retrieval of data using structured queries such as SQL (Structured Query Language). Alternatively, or in addition, communication database 845 may be implemented as a file server providing storage and retrieval of data in the form of files organized as one or more directories, as is well known in the relevant arts.

It should be appreciated that the features described above can be implemented in various embodiments as a desired combination of one or more of hardware, executable modules, and firmware. The description is continued with respect to an embodiment in which various features are operative when executable modules are executed.

9. Digital Processing System

Figure 9:
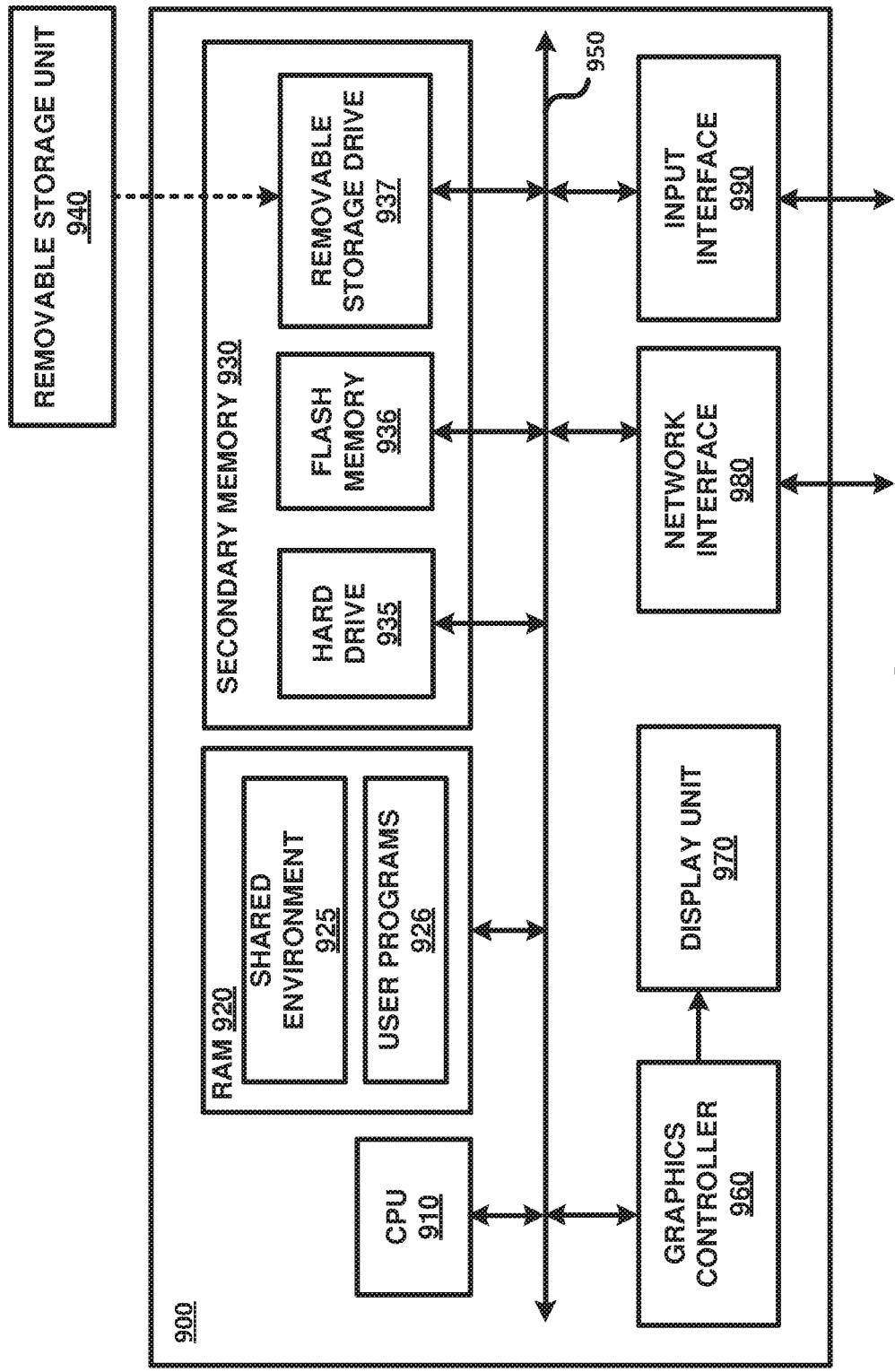
FIG. 9 is a block diagram illustrating the details of digital processing system 900 in which various aspects of the present disclosure are operative by execution of appropriate executable modules.

FIG. 9 is a block diagram illustrating the details of digital processing system 900 in which various aspects of the present disclosure are operative by execution of appropriate executable modules. Digital processing system 900 corresponds to healthcare server 250 or application server 850.

Digital processing system 900 may contain one or more processors such as a central processing unit (CPU) 910, random access memory (RAM) 920, secondary memory 930, graphics controller 960, display unit 970, network interface 980, and input interface 990. All the components except display unit 970 may communicate with each other over communication path 950, which may contain several buses as is well known in the relevant arts. The components of FIG. 9 are described below in further detail.

CPU 910 may execute instructions stored in RAM 920 to provide several features of the present disclosure. CPU 910 may contain multiple processing units, with each processing unit potentially being designed for a specific task. Alternatively, CPU 910 may contain only a single general-purpose processing unit.

RAM 920 may receive instructions from secondary memory 930 using communication path 950. RAM 920 is shown currently containing software instructions constituting shared environment 925 and user programs 926. Shared environment 925 includes operating systems, device drivers, virtual machines, etc., which provide a (common) run time environment for execution of user programs 926.

Graphics controller 960 generates display signals (e.g., in RGB format) to display unit 970 based on data/instructions received from CPU 910. Display unit 970 contains a display screen to display the images defined by the display signals (e.g. portions of the GUI shown in FIG. 4). Input interface 990 may correspond to a keyboard and a pointing device (e.g., touch-pad, mouse) that may be used to provide appropriate inputs (e.g. inputs specified in the user interfaces of FIG. 4). Network interface 980 provides connectivity to a network (e.g., using Internet Protocol), and may be used to communicate with other systems (of FIG. 1) connected to the network.

Secondary memory 930 may contain hard drive 935, flash memory 936, and removable storage drive 937. Secondary memory 930 may store the data (for example, portions of visit summary data of FIG. 5) and software instructions (for implementing the flowchart of FIG. 3 and to provide several features of the present disclosure), which enable digital processing system 900 to provide several features in accordance with the present disclosure. The code/instructions stored in secondary memory 930 either may be copied to RAM 920 prior to execution by CPU 910 for higher execution speeds, or may be directly executed by CPU 910.

Some or all of the data and instructions may be provided on removable storage unit 940, and the data and instructions may be read and provided by removable storage drive 937 to CPU 910. Removable storage unit 940 may be implemented using medium and storage format compatible with removable storage drive 937 such that removable storage drive 937 can read the data and instructions. Thus, removable storage unit 940 includes a computer readable (storage) medium having stored therein computer software and/or data. However, the computer (or machine, in general) readable medium can be in other forms (e.g., non-removable, random access, etc.).

In this document, the term "computer program product" is used to generally refer to removable storage unit 940 or hard disk installed in hard drive 935. These computer program products are means for providing software to digital processing system 900. CPU 910 may retrieve the software instructions, and execute the instructions to provide various features of the present disclosure described above.

The term "storage media/medium" as used herein refers to any non-transitory media that store data and/or instructions that cause a machine to operate in a specific fashion. Such storage media may comprise non-volatile media and/or volatile media. Non-volatile media includes, for example, optical disks, magnetic disks, or solid-state drives, such as secondary memory 930. Volatile media includes dynamic memory, such as RAM 920. Common forms of storage media include, for example, a floppy disk, a flexible disk, hard disk, solid-state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge.

Storage media is distinct from but may be used in conjunction with transmission media. Transmission media participates in transferring information between storage media. For example, transmission media includes coaxial cables, copper wire and fiber optics, including the wires that comprise bus 950. Transmission media can also take the form of acoustic or light waves, such as those generated during radio-wave and infra-red data communications.

Reference throughout this specification to "one embodiment", "an embodiment", or similar language means that a particular feature, structure, or characteristic described in connection with the embodiment is included in at least one embodiment of the present disclosure. Thus, appearances of the phrases "in one embodiment", "in an embodiment" and similar language throughout this specification may, but do not necessarily, all refer to the same embodiment.

Furthermore, the described features, structures, or characteristics of the disclosure may be combined in any suitable manner in one or more embodiments. In the above description, numerous specific details are provided such as examples of programming, software modules, user selections, network transactions, database queries, database structures, hardware modules, hardware circuits, hardware chips, etc., to provide a thorough understanding of embodiments of the disclosure.

10. Conclusion

While various embodiments of the present disclosure have been described above, it should be understood that they have been presented by way of example only, and not limitation. Thus, the breadth and scope of the present disclosure should not be limited by any of the above-described exemplary embodiments, but should be defined only in accordance with the following claims and their equivalents.

It should be understood that the figures and/or screen shots illustrated in the attachments highlighting the functionality and advantages of the present disclosure are presented for example purposes only. The present disclosure is sufficiently flexible and configurable, such that it may be utilized in ways other than that shown in the accompanying figures.

Further, the purpose of the following Abstract is to enable the Patent Office and the public generally, and especially the scientists, engineers and practitioners in the art who are not familiar with patent or legal terms or phraseology, to determine quickly from a cursory inspection the nature and essence of the technical disclosure of the application. The Abstract is not intended to be limiting as to the scope of the present disclosure in any way.

What is claimed is:

1. A method comprising:

forming, via a healthcare system, a visit summary by mapping doctor with patient wherein doctor to patient mapping is updated automatically based on examination of data from external electronic medical record system;

receiving, via the healthcare system, a request to initiate a chat in relation to a patient;

identifying, via the healthcare system, a plurality of healthcare providers having responsibility for the patient from the visit summary;

providing, via the healthcare system, a chat session with the plurality of healthcare providers as participants using corresponding client system;

receiving, via the healthcare system, a command during the chat session, the command requesting information on the patient along with a first authentication token, retrieving information and forwarding the command requesting information on the patient to an integration system;

automatically determining, via the integration system, that the first authentication token is valid and requesting for a second authentication token when the first authentication token is expired;

retrieving, in response to receiving of the command via the healthcare system, an electronic medical record, EMR, of the patient when one of the first authentication token and the second authentication token is valid; and sending, via the healthcare system, the electronic medical record to the participants of the chat session in response to receiving of the command in real-time and when one of the first authentication token and the second authentication token is valid; and wherein the healthcare system is configured to form a consolidated electronic medical record of the patient from retrieved data of the electronic medical record and to perform predictive analysis using predictive algorithms on at least one of the chat, a collaboration history, a chat context, commands given by participants during the chat, and the consolidated electronic medical record of the patient to render treatment suggestions and insights to the participants;

wherein the healthcare system is configured to perform the predictive analytics using the predictive algorithms by searching for symptoms in at least one of the chat, and the collaboration history and arrive at the treatment suggestions and insights regarding at least one of diagnosis that the patient is suffering, and medications for the diagnosis, based on a message by the participants in the chat session;

wherein the chat is automatically integrated with identification number of the patient; and wherein the method is configured to facilitate collaboration among healthcare providers via the healthcare system.

2. The method of claim 1, wherein the command need not specify an identifier of the patient in the chat session.

3. The method of claim 2, wherein the external electronic medical record system maintains the electronic medical record of the patient, the command being received from a first participant, the method further comprising retrieving, via the healthcare system, the electronic medical record of the patient from the electronic medical record system without requiring the first participant to manually authenticate after specifying the command.

4. The method of claim 1, wherein the sending, via the healthcare system, comprises including the electronic medical record of the patient as the message of the chat session; and wherein the electronic medical record of the patient is enabled to be stored as part of a chat history of the chat session in a non-volatile storage.

5. The method of claim 1, further comprising:

receiving, via the healthcare system, an indication to save the chat session;

enabling, via the healthcare system, the participants to edit the message of the chat session to form an edited message; and storing, via the healthcare system, the edited message in a non-volatile storage.

6. A method comprising:

sending, via a client system, a request to initiate a chat in relation to a patient;

participating, via the client system, in a chat session with a plurality of healthcare providers as participants in real-time, the plurality of healthcare providers having responsibility for the patient identified from a visit summary;

sending, via the client system, a command during the chat session, the command requesting information on the patient, wherein the command requesting information on the patient is sent along with a first authentication token via an integration system;

automatically determining that the first authentication token is valid and requesting for a second authentication token when the first authentication token is expired; and wherein in response to the command, an electronic medical record, EMR, of the patient is sent to the participants of the chat session when one of the first authentication token and the second authentication token is valid; and wherein the visit summary is formed by mapping doctor with patient; and wherein doctor/patient mapping is updated automatically based on examination of data from external electronic medical record system; and wherein the electronic medical record of the patient is in a form of a consolidated electronic medical record of the patient; and wherein the chat is automatically integrated with identification number of the patient; and wherein the method comprises facilitating a user to collaborate with healthcare providers via the client system and performing predictive analysis using predictive algorithms on at least one of the chat, a collaboration history, a chat context, commands given by participants during the chat, and the consolidated electronic medical record of the patient to render treatment suggestions and insights to the participants; and wherein the method comprises performing the predictive analytics using the predictive algorithms by searching for symptoms in at least one of the chat, and the collaboration history and arriving at the treatment suggestions and insights regarding at least one of diagnosis that the patient is suffering, and medications for the diagnosis based on a message by the participants in the chat session.

7. The method of claim 6, wherein the user need not specify an identifier of the patient as part of the command.

8. The method of claim 7, wherein the user shares the electronic medical record of the patient without authentication after specifying the command.

9. The method of claim 6, further comprising displaying, via the client system, the electronic medical record of the patient as the message of the chat session; and
  wherein the electronic medical record of the patient is displayed for a pre-configured time period.

10. The method of claim 6, upon receiving an indication to save the chat session, further comprising: sending, from the client system, an edited message for storing in a non-volatile storage, wherein the edited message contains an edited version of the message of the chat session.

11. A tangible non-transitory machine-readable medium comprising instructions executable by one or more processors for implementing one or more operations in a healthcare system for facilitating collaboration among healthcare providers, the operations comprising:
  forming, via the healthcare system, a visit summary by mapping doctor with patient wherein doctor/patient mapping is updated automatically based on examination of data from external electronic medical record system;
  receiving, via the healthcare system, a request to initiate a chat in relation to a patient;
  identifying, via the healthcare system, a plurality of healthcare providers having responsibility for the patient from the visit summary;
  providing, via the healthcare system, a chat session with the plurality of healthcare providers as participants using corresponding client system;
  receiving, via the healthcare system, a command during the chat session, the command requesting information on the patient along with a first authentication token, retrieving information, and forwarding the command requesting information on the patient to an integration system;
  automatically determining, via the integration system, that the first authentication token is valid and requesting for a second authentication token when the first authentication token is expired;
  retrieving, in response to receiving of the command, via the healthcare system, an electronic medical record, EMR, of the patient when one of the first authentication token and the second authentication token is valid; and
  sending, via the healthcare system, the electronic medical record to the participants of the chat session in response to receiving of the command in real-time and when one of the first authentication token and the second authentication token is valid; and
  wherein the chat is automatically integrated with identification number of the patient;
  wherein the healthcare system is configured to form a consolidated electronic medical record, of the patient from retrieved data of the electronic medical record and to perform predictive analysis using predictive algorithms on at least one of the chat, a collaboration history, a chat context, commands given by participants during the chat, and the consolidated electronic medical record of the patient to render treatment suggestions and insights to the participants; and
  wherein the healthcare system is configured to perform the predictive analytics using the predictive algorithms by searching for symptoms in at least one of the chat, and the collaboration history and arrive at the treatment suggestions and insights regarding at least one of diagnosis that the patient is suffering, and medications for the diagnosis, based on a message sent by the participants in the chat session.

12. The non-transitory machine-readable medium of claim 11, wherein the command need not specify an identifier of the patient in the chat session.

13. The non-transitory machine-readable medium of claim 12, wherein the external electronic medical record system maintains the electronic medical record of the patient, the command being received from a first participant, the operations further comprising retrieving, via the healthcare system, the electronic medical record of the patient from the external electronic medical record system without requiring the first participant to manually authenticate after specifying the command.

14. The non-transitory machine-readable medium of claim 11, wherein the sending comprises including, via the healthcare system, the electronic medical record of the patient as the message of the chat session; and wherein the electronic medical record of the patient is enabled to be stored as part of a chat history of the chat session in a non-volatile storage.

15. The non-transitory machine-readable medium of claim 11, the operations further comprising:
  receiving, via the healthcare system, an indication to save the chat session;
  enabling, via the healthcare system, the participants to edit the message of the chat session to form an edited message; and storing, via the healthcare system, the edited message in a non-volatile storage.

16. A digital processing system comprising:
  a memory to store instructions;
  one or more processors to execute the instructions stored in the memory to cause the digital processing system to perform actions of:
  forming a visit summary by mapping doctor with patient wherein doctor to patient mapping is updated automatically based on examination of data from external electronic medical record system;
  receiving a first request for healthcare providers associated with a patient to initiate a chat in relation to the patient;
  identifying a plurality of healthcare providers having responsibility for the patient from the visit summary;
  sending the plurality of healthcare providers as being associated with the patient to facilitate a chat session to be provided with the plurality of healthcare providers as participants using corresponding client system;
  receiving second request for information on the patient in response to a command, during the chat session, along with a first authentication token via an integration system;
  automatically determining that the first authentication token is valid and requesting for a second authentication token when the first authentication token is expired;
  retrieving, in response to receiving of the second request for the information on the patient, via the digital processing system, an electronic medical record, EMR, of the patient when one of the first authentication token and the second authentication token is valid; and
  sending the electronic medical record in response to be receiving of the second request to facilitate the electronic medical record of the patient to be provided to the participants of the chat session when one of the first authentication token and the second authentication token is valid; and
  wherein the digital processing system is configured to form a consolidated electronic medical record of the patient from retrieved data of the electronic medical record and to perform predictive analysis using predictive algorithms on at least one of the chat, a collaboration history, a chat context, commands given by participants during the chat, and the consolidated electronic medical record of the patient to render treatment suggestions and insights to the participants; and wherein the digital processing system is configured to perform the predictive analytics using the predictive algorithms by searching for symptoms in at least one of the chat, and the collaboration history and arrive at the treatment suggestions and insights regarding at least one of diagnosis that the patient is suffering, and medications for the diagnosis based on a message by the participants in the chat session; and wherein the chat is automatically integrated with identification number of the patient;

and wherein the digital processing system is configured to facilitate collaboration among healthcare providers.

17. The digital processing system of claim 16, wherein the command is received from a first participant and does not specify an identifier of the patient in the chat session, wherein the electronic medical record is retrieved without requiring the first participant to manually authenticate after specifying the command.

18. The digital processing system of claim 16, wherein the electronic medical record of the patient is displayed as part of the chat session for a pre-configured time period.

19. The digital processing system of claim 16, wherein the digital processing system is an insurance server belonging to an insurance carrier, the insurance server maintaining information on patients having insurance coverage with the insurance carrier.

20. The digital processing system of claim 16, wherein the digital processing system is an enterprise server belonging to a third-party enterprise.

* * * * *